(12) United States Patent
Nisal et al.

(10) Patent No.: US 11,046,737 B2
(45) Date of Patent: Jun. 29, 2021

(54) HIGHLY CRYSTALLINE SPHERICAL SILK FIBROIN MICRO-PARTICLES AND A PROCESS FOR PREPARATION THEREOF

(71) Applicant: Council of Scientific and Industrial Research, New Delhi (IN)

(72) Inventors: Anuya Amol Nisal, Pune (IN); Premnath Venugopalan, Pune (IN); Bhakti Dnyaneshwar Khude, Pune (IN)

(73) Assignee: COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 15/541,805

(22) PCT Filed: Jan. 6, 2016

(86) PCT No.: PCT/IN2016/050002
§ 371 (c)(1),
(2) Date: Jul. 6, 2017

(87) PCT Pub. No.: WO2016/110873
PCT Pub. Date: Jul. 14, 2016

(65) Prior Publication Data
US 2018/0273592 A1    Sep. 27, 2018

(30) Foreign Application Priority Data
Jan. 6, 2015 (IN) .......................... 0045/DEL/2015

(51) Int. Cl.
| | |
|---|---|
| C07K 14/435 | (2006.01) |
| A61L 27/22 | (2006.01) |
| A61K 8/02 | (2006.01) |
| A61K 8/98 | (2006.01) |
| A61K 9/16 | (2006.01) |
| C08L 89/00 | (2006.01) |
| A61Q 19/00 | (2006.01) |
| C08H 1/00 | (2006.01) |

(52) U.S. Cl.
CPC ........ *C07K 14/43586* (2013.01); *A61K 8/025* (2013.01); *A61K 8/987* (2013.01); *A61K 9/1658* (2013.01); *A61K 9/1694* (2013.01); *A61L 27/227* (2013.01); *A61Q 19/00* (2013.01); *C08H 1/00* (2013.01); *C08L 89/00* (2013.01); *A61K 2800/10* (2013.01); *A61K 2800/28* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 8,361,617 B2 * | 1/2013 | Kaplan | A61L 27/227 428/357 |
| 2015/0174256 A1 * | 6/2015 | Kaplan | A43B 1/02 424/443 |

FOREIGN PATENT DOCUMENTS

| | | | |
|---|---|---|---|
| CN | 10334117 | * | 6/2013 |
| CN | 103341175 | * | 6/2013 |
| WO | 93/15244 | | 8/1993 |
| WO | 2014/125505 | | 8/2014 |

OTHER PUBLICATIONS

Wang et al. "Nanolayer Biomaterial Coatings of Silk Fibroin for Controlled Release" 2007.*
Lv et al. "Preparation of 3-D regenerated fibroin scaffolds with freeze drying method and free drying/foaming technique" 2006.*
Carteret al. "Measurement of particle shape using digital imaging techniques". 2005.*

* cited by examiner

*Primary Examiner* — Danah Al-Awadi
(74) *Attorney, Agent, or Firm* — Carmody Torrance Sandak & Hennessey LLP

(57) ABSTRACT

The present invention provides silk fibroin micro-particles having a high crystallinity index (1.3-1.5) and low sphericity index (≤0.01) and a process for the preparation thereof. The high crystallinity index confers longer degradation periods to the instant silk fibroin micro-particles, therefore facilitating their use in biomedical applications.

17 Claims, 3 Drawing Sheets

HIGHLY CRYSTALLINE SPHERICAL SILK FIBROIN MICRO-PARTICLES AND A PROCESS FOR PREPARATION THEREOF

FIELD OF THE INVENTION

The present invention relates to crystalline, spherical silk fibroin micro-particles having high crystallinity index and a low sphericity index and a process for the preparation thereof. Further, the present invention relates to a composition comprising spherical and highly crystalline silk fibroin micro-particles for use in biomedical applications.

BACKGROUND AND PRIOR ART OF THE INVENTION

Silk fibroin (SF) is a natural polymer produced by a variety of insects and spiders. Dragline silk from the spider *Nephila clavipes* and cocoon silk from the domesticated silkworm *Bombyx mori*, are the best characterized silk which have been used in textile production, clinical sutures and more recently employed as scaffolds for tissue regeneration on account of the extraordinary mechanical properties such as high tensile strength and extensibility, as well as reported biological compatibility.

Silk fibre from a silkworm cocoon consists of two filaments: the fibroin brins, and glue like, soluble rich gum sericin that binds the fibroins together. One cocoon can comprise 3,500 million of single fibre with filaments 15-25 µm thick (Robson 1985). When processing silk for textile use, sericin is removed by hot water during the degumming process and the fibres, now single fibroin filaments, are spun into a thread.

Structurally, SF is characterized by repetitive hydrophobic and hydrophilic peptide sequences and consists of heavy and light chain polypeptides, linked by a disulfide bond at the C-terminus of the two subunits. The primary structure of *Bombyx mori* SF protein is characterized by the presence of three amino acids glycine, alanine, and serine roughly in a ratio of 3:2:1. SF chains also contain amino acids with bulky and polar side chains, in particular tyrosine, valine and acidic amino acids. The repetitive sequence in hydrophobic amino acid residues dominates the β-sheet structure, forming crystalline regions in SF fibers. The formation of these β-sheets results in insolubility in water.

Moreover, compared to other proteins, silk has a relatively high degree of crystallinity with fibroin β-sheet crystallites aligned along the fibre axis. The crystalline regions account for the high tensile and tear strength characteristic of silk fibres (Timar-Balazsy and Eastop 1998). The amorphous regions are more open to all sorts of agents that cause alteration such as oxygen, humidity and salts, and other studies have shown that silk deterioration starts here (Crighton 1993).

A research study centred on 'Surveying silk fibre degradation by crystallinity determination" by Susanne Greiff et al. focuses on determination of silk fibres crystallinity and its relation to the ageing process. The investigators study that the silk fiber is highly crystalline and the crystalline regions in a silk protein polymer may remain intact even if degradation processes have already caused a loss of integrity and decreased mechanical performance. In the final stages of deterioration, when degradation is sufficiently severe, the crystalline regions are affected.

U.S. Pat. No. 5,252,285 relates to a process for synthesis of silk fibroin fibers. The process which comprises forming silk fibroin solution in an aqueous salt solution followed by removal of salt and water by dialysis from the fibroin solution to form a silk fibroin material; forming a fiber-spinnable solution comprising about 5 to 25% by weight of the silk fibroin material in hexafluoroisopropanol; and extruding the fiber-spinnable solution through a spinneret to form silk fibroin fibers.

In recent years, the reported exceptional nature of silk has led to increased interest in silk for biomedical applications. However, the use of silk fibroin micro-particles is considered more favorable and convenient due to their characters of porosity, particle size, flexibility, crystallinity and their ability to fuse to form silk fibroin scaffolds.

Several different protocols have been reported for preparation of silk fibroin particles, a few of the methods are as follows:

The inventors of the instant invention in PCT International Publication WO2014125505 describe a novel process for preparation of silk fibroin scaffolds by fusing together particles of silk fibroin. The scaffolds so formed have several advantages over other existing scaffolds in terms of pore size and pore size distribution, scaffold porosity, controlled biodegradability, excellent mechanicals and flexibility to load in variety of fillers, drug molecules, etc. The silk particles described therein are prepared by freezing, lyophilizing and annealing them to get the required properties.

However, the process used is time consuming and tedious, although it confers flexibility in terms of the required properties for the scaffold. The crystallinity index obtained in WO'505 is 0.78 to 1.3, therefore there is further scope in the art to increase the crystallinity of silk fibroin. The particles synthesized have a lower crystallinity index; therefore have a shorter degradation time and hence are not favorable for biomedical applications requiring longer degradation time.

Also, it is extremely desirable to produce spherical particles for micro-particle scaffold applications as spherical particles randomly close pack to give about 46% porosity in the scaffolds. Non-spherical particles can be further tightly packed reducing the porosity in the scaffold (Donev, Cisse, Sachs, Torquato, & Chaikin, 2004, Improving the Density of Jammed Disordered Packings Using Ellipsoids, 303, *Science*, 990-993.) The reduction in porosity hampers the performance of scaffolds in cell culture applications.

The present invention provides a cost-effective process resulting in the formation of microparticles prepared using SF-HFIP solutions dispensed at a controlled rate into a methanol coagulant bath. The microparticles obtained using these processes are highly crystalline and spherical.

Based on the prior art study, it is clear that producing spherical particles of high sphericity and very high crystallinity using the process of the invention is unknown. Furthermore, it is surprising that this process produces particles of very high crystallinity index (>1.3) as compared to methods previously reported in WO2014125505.

OBJECTS OF THE INVENTION

Main object of the present invention is to provide crystalline, spherical silk fibroin micro-particles having high crystallinity index and a low sphericity index.

Another object of the present invention is to provide a process for the preparation crystalline, spherical silk fibroin micro-particles useful in biomedical applications.

SUMMARY OF THE INVENTION

Accordingly, present invention provides spherical, highly crystalline silk fibroin (SF) particles having crystallinity index in the range of 1.3-1.5 and sphericity index in the range of 0.029- to 0.01 mm.

In an embodiment of the present invention, mean particle size of the SF particles is in the range of 400-1000μ.

In another embodiment of the present invention, said particles are useful in the preparation of 3D silk fibroin scaffolds for biomedical applications.

In yet another embodiment of the present invention, 3D silk fibroin scaffolds formed by fusing SF micro particles retain 90% of its weight after a period of 4 days in an invitro 1 U/ml proteolytic degradation experiment.

In yet another embodiment, present invention provides a process for the preparation of spherical, highly crystalline silk fibroin (SF) comprising the steps of:
  a) lyophilizing 3 to 5 wt % regenerated silk fibroin solution (RSF) prepared in water at a temperature in the range of −45 to −60° C. for period in the range of 6-8 h to obtain silk fibroin powder;
  b) dissolving silk fibroin powder as obtained in step (a) in hexafluoroisopropanol (HFIP) to obtain 5-7 wt % SF solution;
  c) coagulating the SF solution as obtained in step (b) in a methanol bath to obtain silk fibroin (SF) particles.

In yet another embodiment, present invention provides a composition comprising spherical, highly crystalline silk fibroin particles as claimed in claim 1 optionally along with additives.

In yet another embodiment of the present invention, the additive present is in the range of 1-70% by weight.

In yet another embodiment of the present invention, the additive is selected from the group consisting of ceramic fillers such as hydroxyapatite, beta tricalcium phosphate, calcium sulphate, calcium phosphates, etc. or natural and synthetic fiber reinforcements such as SF fibers, jute fibers, polypropylene fibers or other biomolecules such as drugs, growth factors.

In yet another embodiment of the present invention, said composition is a gel, hydrogel, a paste, a lotion, a cream, an ointment, a foam, a spray, an aerosol, a scrub, or any combinations thereof.

DETAILED DESCRIPTION OF THE INVENTION

The present invention provides highly crystalline and spherical silk fibroin micro-particles having a size of 400-1000 μm and crystallinity index in the range of 1.3-1.5.

In an aspect, the present invention provides a process for the preparation of highly crystalline and spherical silk fibroin particles characterized in that the particles have crystallinity index in the range of 1.3-1.5 and sphericity index<0.01 comprising the steps of:
  a) lyophilizing regenerated silk fibroin solution (RSF) prepared in water to obtain silk fibroin powder;
  b) dissolving silk fibroin powder in hexafluoroisopropanol (HFIP) to obtain 6-7 wt % SF in HFIP solution; and
  c) coagulating the solution obtained in step (b) in a methanol bath to obtain silk fibroin microparticles.

Preferably, at concentrations ranging from 6 to 7 wt % of the silk fibroin in HFIP solution spherical silk fibroin particles are obtained.

In another aspect, the present invention provides highly crystalline silk-fibroin micro-particles having crystallinity index in the range of 1.3-1.5.

In yet another aspect, the present invention provides a composition comprising highly crystalline silk fibroin micro-particles, with or without additives characterized in that the particles have a crystallinity index in the range of 1.3-1.5.

Advantageously, the instant silk fibroin particles have improved mechanical stability and longer degradation period when used in the preparation of scaffolds for use in biomedical applications and tissue engineering.

Present invention provides process for the preparation of spherical, highly crystalline silk fibroin particles which comprises preparing the RSF solution employed in step (a) in water and subjecting it to lyophilization to derive silk fibroin powder. Lyophilization of 40-100 ml of 3 to 5 wt % regenerated silk fibroin solution in step (a) is carried out at a temperature ranging from −45 to −60° C. for 8-24 h to obtain about 120-150 mg of silk fibroin.

Further, fibroin silk powder derived in step (a) is dissolved in HFIP solvent to obtain a solution. This solution obtained in step (b) is filled in a syringe equipped with a needle which is mounted on a syringe pump and the solution is pumped out at a constant flow rate in the range of 0.1-0.5 ml/min. The drops formed at the needle tip of the syringe are allowed to fall into a methanol bath maintained at least 15-40 cm below the pump. The rate at which the drop falls into the coagulant bath is controlled in the range of 0.05 to 2 ml/min. The silk fibroin particles, obtained from the drops, are kept in the coagulant bath for a period of at least 24 hrs before removing followed by air drying for capturing the image.

Figure 1:
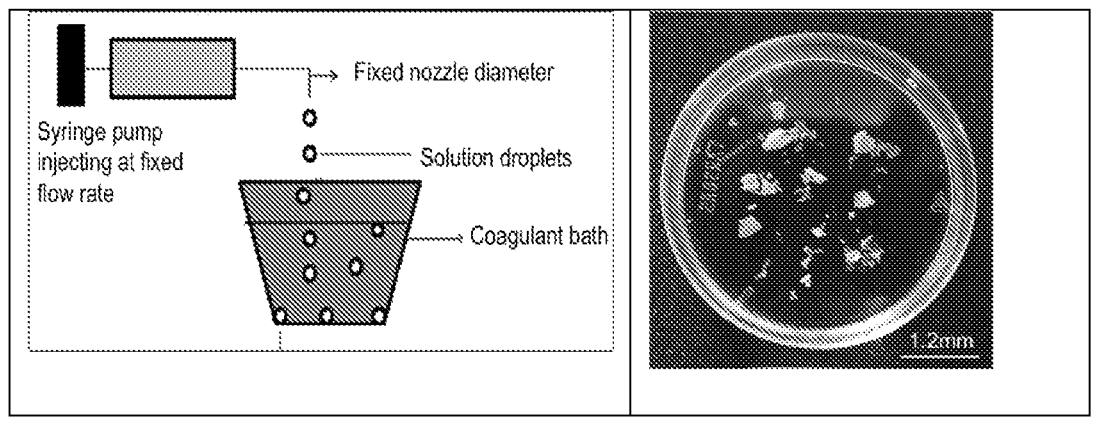
FIG. 1(a) depicts the schematic for preparation of silk particles and (b) depicts silk fibroin particles as obtained in the coagulant bath.

The needle employed in the syringe is preferably a 26 G (Gauge) needle wire. The internal diameter of the nozzle is in the range of 0.1 to 0.6 mm. The entire assembly of the syringe fitted to a nozzle and the methanol coagulant bath is depicted in FIG. 1 (a) of the instant invention.

The present invention provides the lyophilization of 50 ml of 3 wt % regenerated silk fibroin solution in step (a) carried out at a temperature ranging from −45 to −60° C. for 8 h to obtain about ~140 mg of silk fibroin powder.

Spherical, highly crystalline silk-fibroin micro-particles are obtained by subjecting 5-7 wt % of SF solution in HFIP to coagulation in methanol.

Preferably, at concentrations ranging from 6-7 wt % of the silk fibroin in HFIP solution spherical silk fibroin particles are obtained.

The present invention provides crystalline, spherical silk fibroin particles having sphericity index in the range of 0.029 to 0.01 mm.

A sphericity index closer to zero indicates more spherical particles. This reduced sphericity index for the particles produced using the 6 and 7 wt % solution indicates that these particles are more spherical than those produced by 3, 4 or 5 wt % solution of silk fibroin in HFIP.

The instant spherical and highly crystalline micro-particles are randomly closely packed to give about 40-50% porosity in the scaffolds.

The silk fibroin particles are characterized in that having a mean particle size in the range of 400-1000μ.

The instant spherical, crystalline silk fibroin particles are used in the preparation of 3D scaffolds, which may be used in biomedical applications thus conferring longer degradation period.

SF micro particles prepared using 6 wt % HFIP solutions (Described in Example 4) are used in the preparation of 3D cylindrical scaffolds. The particles were dipped in 3-5 wt % regenerated silk fibroin solution and packed in a cylindrical mold. An additional 20 μl of RSF solution was added to the mold, thereafter placing the mold in a convection oven at 60° C. for 2 h resulting in the particles fusing together to form a 3D silk fibroin scaffold.

The 3D scaffold generated is subjected to enzymatic degradation to determine the stability of the instant spherical, crystalline micro-particles prepared by the present process.

The 3D silk fibroin scaffold formed by fusing SF micro-particles retain more than 90% of its weight after a period of 4 days.

Figure 6:
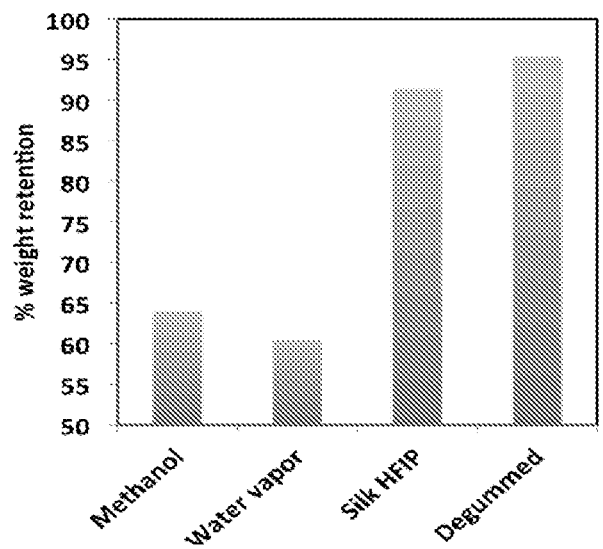
FIG. 6 depicts % weight retention as per in vitro degradation studies showing improved degradation of scaffolds prepared with highly crystalline SF microparticles as compared with water annealed and methanol annealed SF particle scaffolds.

The 3D silk fibroin scaffolds are incubated in 1 U/ml of Protease XIV solution at 37° C. for 4 days with replacing of the enzyme solution every 24 h. Pure degummed silk fibroin fibers are employed as a control. The weight of the samples retained after 4 days is measured and the same is depicted in FIG. 6. Further, FIG. 6 also shows the weight retention for porous scaffolds prepared using water annealed and methanol annealed particles prepared in WO'505.

The scaffold prepared using the instant synthesized spherical and highly crystalline micro-particles retains more than 90% of its weight after degradation and its performance is comparable to that of the highly crystalline silk fibroin fibers. These values are significantly better than those observed for water annealed and methanol annealed particle scaffolds (WO2014125505).

The present invention provides a composition comprising highly crystalline silk fibroin particles having crystallinity index in the range of 1.3-1.5, with or without additives.

Further, the composition comprises one or more additives wherein the additive is present in the range of 1-70% by weight.

The additives are selected from the group consisting of ceramic fillers such as hydroxyapatite, beta tricalcium phosphate, calcium sulphate, calcium phosphates, or natural and synthetic fiber reinforcements such as SF fibers, jute fibers, polypropylene fibers or other biomolecules such as drugs or growth factors.

Accordingly, hydroxyapatite nanoparticles are mixed in a solution of silk fibroin in HFIP.

The concentration of silk fibroin in HFIP is in the range of 6-7 wt %.

The ratio of SF:HFIP used in the preparation of the instant composition is in the range of 0.5-1 to 2:2.5, preferably, the ratio of SF:HFIP is 1:1.5.

Further, the composition is a gel or hydrogel, a paste, a lotion, a cream, an ointment, a foam, a spray, an aerosol, a scrub, or any combinations thereof.

EXAMPLES

Following examples are given by way of illustration therefore should not be construed to limit the scope of the invention.

Example 1

Preparation of Silk Fibroin Particles from Regenerated Silk Fibroin Solution and Methanol Coagulant Bath 3 wt % RSF solution was filled in a syringe equipped with a 26 G needle. The syringe was mounted on a syringe pump and the solution was pumped out at a constant flow rate of 0.1 ml/min. The drops formed at the needle tip were allowed to fall into a methanol bath kept at least 20 cm below. It was observed that no particles of silk fibroin could be formed as the drop disintegrates into this coagulant bath. The protocol and the results are depicted in FIG. 1 (*b*). The silk fibroin was kept immersed in the methanol bath for 24 h before removing followed by air drying for capturing the image.

Example 2

Figure 2:
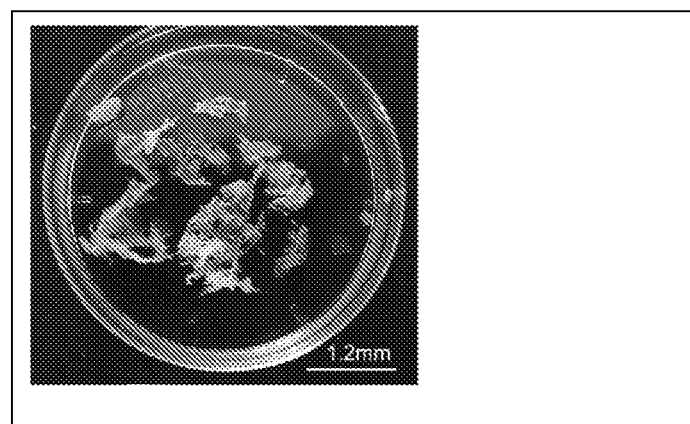
FIG. 2 depicts silk fibroin micro-particles obtained in coagulant bath.

Preparation of Silk Fibroin Particles from Silk Fibroin Solution in Formic Acid and Methanol Coagulant Bath The regenerated silk fibroin solution is lyophilized for 8 h at −45 to −60° C. to obtained SF powder. This powder is used to prepare a 3 wt % solution of silk fibroin in formic acid. This solution is used to make particles of silk fibroin as described in Example 1. It is observed that no particles of silk fibroin can be formed as the drop disintegrates into this coagulant bath and agglomerates below. An image of the silk fibroin obtained is shown in FIG. 2.

Example 3

Figure 3A:
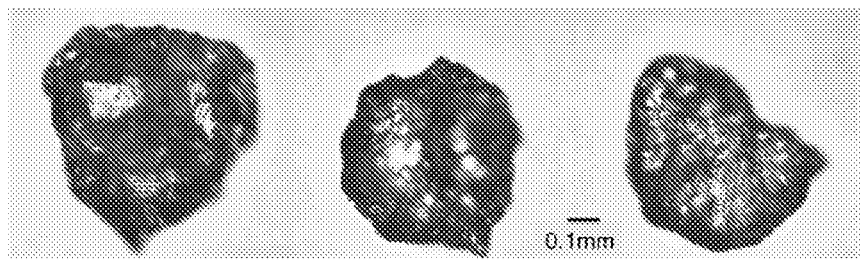
FIG. 3(a) depicts optical micrographs of SF microparticles obtained in Example 3.
Figure 3B:
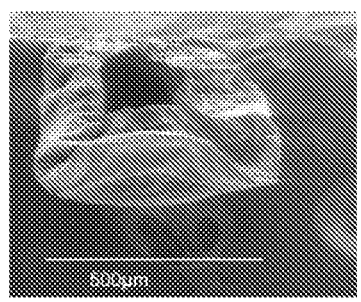
FIG. 3(b) Scanning electron micrographs of SF microparticles obtained in Example 3.

Preparation of Silk Fibroin Particles from Silk Fibroin Solution in Hexfluoroisopropanol and Methanol Coagulant Bath The regenerated silk fibroin solution is lyophilized for 8 h at −45 to −60° C. to obtained SF powder. This powder is used to prepare a 3 wt % solution of silk fibroin hexafluroisopropanol. This solution was used to make particles of silk fibroin as described in Example 1. It is observed that particles of silk fibroin can be formed continuously using this protocol. An image of the silk fibroin particles obtained is shown in FIGS. 3*a* and *b*. The particles obtained are not exactly spherical in shape and have pore of ~250 μm at the centre. The mean particle size obtained is 0.51 mm with a % Std. Dev of 9.24. The silk fibroin molecules in the particles exhibit predominant beta sheet structures as is evident from the crystallinity index, calculated as described in copending application No. 0421DEL2013.

TABLE 1

Statistical data after image analysis done on particles prepared using process described in 0

| | |
|---|---|
| Mean particle diameter (mm) | 0.51 |
| % Standard deviation | 9.24 |
| d10 | 0.45 |
| d50 | 0.50 |
| d90 | 0.57 |
| d10/d90 | 0.93 |
| Intra-particle porosity* (%) | 33.89 |
| Crystallinity index (Std. dev)** | 1.48 (0.06) |

*Theoretical Calculated Porosity = $\frac{V_1 - V_2}{V_1} * 100$ where $V_1$ = Measured Volume = $\frac{4\pi r^3}{3}$ and $V_2 = w/\rho$ such that r is the radius of particle measured by image analysis, w is the weight of a single particle and ρ is density of crystalline silk = 1.4 g/cm3
**Crystallinity Index = Ratio of areas of crystalline beta sheet peaks (1616-1621, 1622-1627, 1628-1637 cm-1) to ratio of random coil peaks (1638-1646 and 1647-1655 cm-1) as obtained after peak deconvolution and curve fitting of Infrared spectra in amide I region

Example 4

Figure 4:
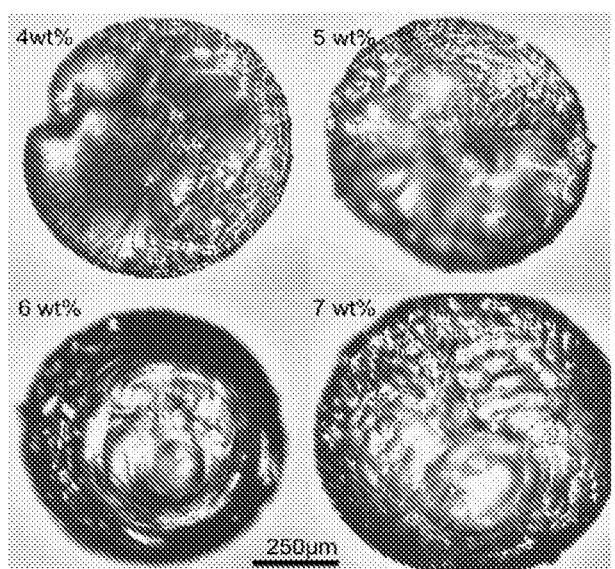
FIG. 4 depicts silk fibroin particles obtained from different concentrations of SF solutions in hexafluoroisopropanol (HFIP) using a methanol coagulant bath.

Preparation of Silk Fibroin Particles from Silk Fibroin Solution in Hexfluoroisopropanol and Methanol Coagulant Bath 4, 5, 6, 7 and 8 wt % solutions of silk fibroin were prepared in hexafluroisopropanol. These solutions were used to make particles of silk fibroin as described in Example 1. It is observed that particles of silk fibroin can be formed continuously using this protocol except for the 8 wt % solution. The 8 wt % solution is too viscous to form any particles. Representative optical microscopy images of the silk fibroin particles obtained using these solutions is shown in FIG. 4. The particles obtained are fairly spherical in shape for the 5, 6 and 7 wt % sample and more so for the 6 and 7 wt % sample. The particle size increases with increasing the SF concentration as is shown by the data obtained after image analysis on particles in Table 2.

TABLE 2

Statistical data after image analysis done on particles prepared using process described in example 4

| | Concentration of SF in HFIP | | | | |
|---|---|---|---|---|---|
| | 3 wt % | 4 wt % | 5 wt % | 6 wt % | 7 wt % | 8 wt % |
| Mean particle diameter (mm) | 0.51 | 0.66 | 0.69 | 0.75 | 0.80 | Particles could not be made |
| % Standard deviation | 9.24 | 7.28 | 5.68 | 10.77 | 6.34 | |
| d10 | 0.45 | 0.6 | 0.64 | 0.62 | 0.71 | |
| d50 | 0.50 | 0.67 | 0.69 | 0.76 | 0.8 | |
| d90 | 0.57 | 0.71 | 0.74 | 0.85 | 0.86 | |
| d10/d90 | 0.93 | 0.85 | 0.86 | 0.93 | 0.83 | |
| Sphericity index (mm) | 0.042 | 0.034 | 0.029 | 0.010 | 0.010 | |

Example 5

Comparison of Spherical Nature of Particles Prepared in Example 3 and Example 4

Figure 5:
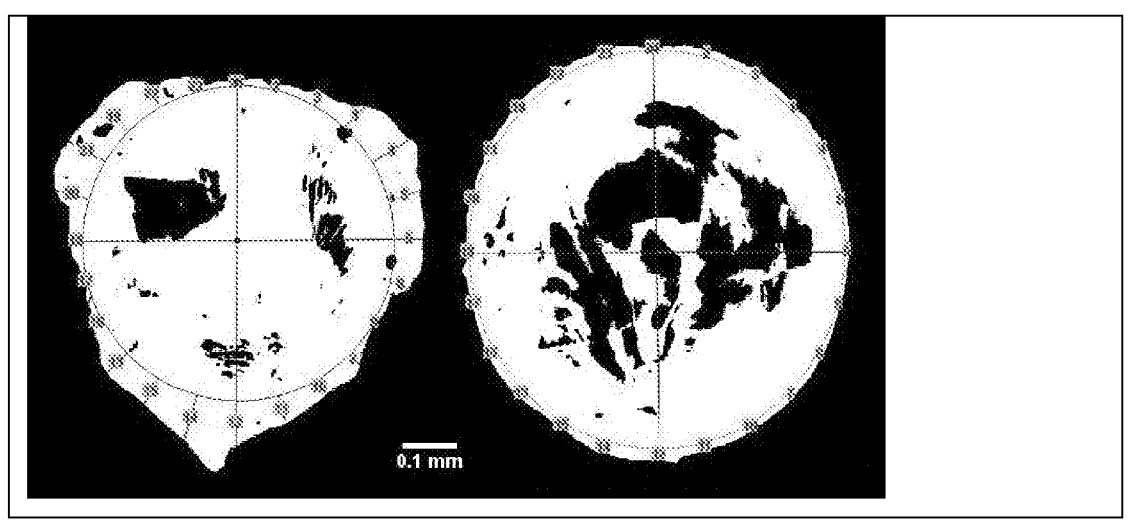
FIG. 5 depicts Sphericity index measurement of SF microparticles and comparison of the spherical nature of silk fibroin particles based on image analysis using optical microscope on 3 wt % and 6 wt % particles prepared in Example 3 and Example 4.

The particles prepared using 3 and 6 wt % SF solutions in HFIP demonstrated in Example 3 and Example 4 respectively were imaged on an optical microscope and image analysis was done using Image J software. A largest possible circle was fitted inside each particle as shown in FIG. 5. The distance between the fitted circle and the original particle boundary was measured at 24 different locations along the circumference of the circle. The average distance measured was 0.042 mm and 0.01 mm for the particles prepared in Example 3 and Example 4 respectively. This number is called the sphericity index. A sphericity index closer to zero indicates more spherical particles. The sphericity index for particles prepared in Example 3 and Example 4 is tabulated in Table 2. This reduced sphericity index for the particles produced using the 6 and 7 wt % solution indicates that these particles are more spherical than those produced by 3, 4 or 5 wt % solution of silk fibroin in HFIP.

Example 6

Improved Degradation Resistance in Scaffolds

The particles prepared using 6 wt % HFIP solutions as described in example 4 were used to prepare 3D cylindrical scaffolds. Briefly, the particles were dipped in 3 wt % regenerated silk fibroin solution and filled in a mold. An additional 20 μl of RSF solution was added to the mold. The mold was placed in a convection oven at 60° C. for 2 h. The particles fused together to form a 3D scaffold and this scaffold was later used for enzymatic degradation experiment. The scaffold was incubated in 1 U/ml of Protease XIV solution at 37° C. for 4 days. The enzyme solution was replaced every 24 h. Pure degummed silk fibroin fibers were used as a control. The weight of the samples retained after 4 days was measured and is FIG. 6 shows the same. FIG. 6 also shows the weight retention for porous scaffolds prepared using water annealed and methanol annealed particles prepared in WO'505. As can be seen from the figure, the scaffold retains more than 90% of its weight after degradation and its performance is comparable to that of the highly crystalline silk fibroin fibers. These values are significantly better than those observed for water annealed and methanol annealed particle scaffolds.

Example 7

Incorporation of Additives

Figure 7:
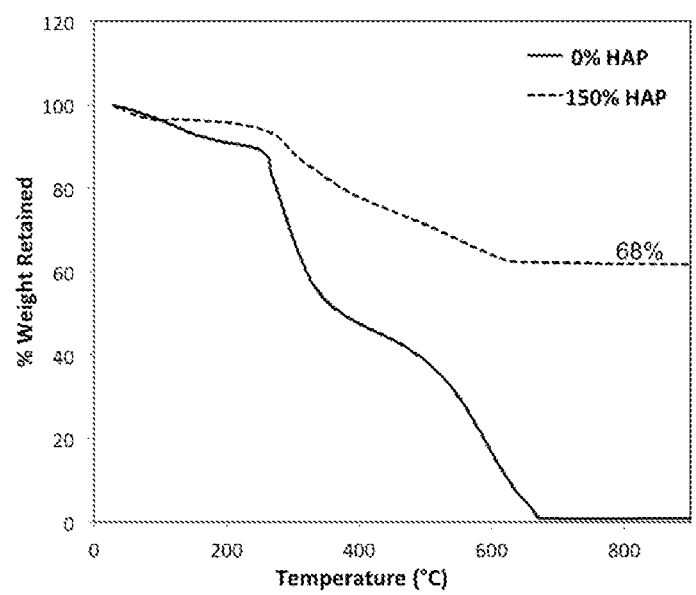
FIG. 7 depicts thermo-gravimetric data for the instant SF micro-particles prepared with and without HFIP loading and shows incorporation of filler such as hydroxyapatite into the highly crystalline SF micro-particles.

This example demonstrated the flexibility of the process to incorporate other additives such as fillers into these highly crystalline micro particles. Hydroxyapatite (HAP) nanoparticles (Sigma Aldrich) were mixed in 6 wt % solution of silk fibroin in HFIP. The ratio of SF:HFIP used was 1:1.5 for this example. Microparticles were formed as per the protocol described in Example 4. FIG. 7 shows thermogravimetric data for these SF microparticles prepared with and without HFIP loading. It may be seen here that HAP is incorporated into these microparticles and it amounts to at least 70% by weight.

ADVANTAGES OF THE INVENTION

- Silk fibroin particles are obtained using lesser number of processing steps,
- Smaller particles can be easily prepared by changing concentration, thus is advantageous for making thinner scaffolds, and
- Silk fibroin particles are highly crystalline,
- High crystallinity of the silk fibroin particles confer longer degradation time, and therefore may be used in scaffold in the area of tissue engineering and other biomedical applications requiring prolonged degradation.

Particles obtained are highly spherical.

Spherical particles randomly close pack to give about 46% porosity in the scaffolds. Non-spherical particles can be further tightly packed reducing the porosity in the scaffold (Donev, Cisse, Sachs, Torquato, & Chaikin, 2004, Improving the Density of Jammed Disordered Packings Using Ellipsoids, 303 (February), 990-993.)

The invention claimed is:

1. Spherical, highly crystalline silk fibroin (SF) particles, wherein said SF particles have a crystallinity index in the range of 1.3-1.5, an aspect ratio of less than 1.08, and a sphericity index in the range of 0.01 to 0.029 mm, wherein said sphericity index is a measure of the deviation/variation from a perfect sphere and is determined by fitting a largest possible circle inside a particle boundary of an imaged SF particle and measuring a distance between the fitted circle and the particle boundary at locations along the circumference of the circle and calculating an average of the measured distances, wherein said particles are fused together to form 3D silk fibroin scaffolds, said fused 3D silk fibroin scaffolds retain at least 90% of their weight after a period of 4 days in an in vitro 1 U/ml proteolytic degradation experiment;

wherein said SF particles are prepared by dissolving 5-7 wt. % of silk fibroin powder in hexafluoroisopropanol (HFIP), said powder obtained by lyophilizing 3-5 wt. % regenerated silk fibroin solution.

2. The spherical, highly crystalline silk fibroin particles as claimed in claim 1, wherein mean particle size of the SF particles is in the range of 400-1000μ.

3. The spherical, highly crystalline silk fibroin particles as claimed in claim 1, wherein said particles are useful in the preparation of 3D silk fibroin scaffolds for biomedical applications.

4. A process for the preparation of spherical, highly crystalline silk fibroin (SF) particles comprising the steps of:
   a) lyophilizing 3 to 5 wt % regenerated silk fibroin solution (RSF) prepared in water at a temperature in the range of −45 to −60° C. for period in the range of 6-8 h to obtain silk fibroin powder;
   b) dissolving silk fibroin powder as obtained in step (a) in hexafluoroisopropanol (HFIP) to obtain 5-7 wt % SF solution;
   c) coagulating the SF solution as obtained in step (b) in a methanol bath to obtain silk fibroin (SF) particles;
   d) fusing the SF particles together to form 3D silk fibroin scaffolds, wherein the 3D silk fibroin particles retain at least 90% of their weight after a period of 4 days in an invitro 1 U/ml proteolytic degradation experiment; and wherein said SF particles have a crystallinity index in the range of 1.3-1.5, and an aspect ratio of less than 1.08, and a sphericity index in the range of 0.029- to 0.01 mm,
   wherein said sphericity index is determined by fitting a largest possible circle inside a particle boundary of an imaged SF particle and measuring a distance between the fitted circle and the particle boundary at locations along the circumference of the circle and calculating an average of the measured distances.

5. A composition comprising spherical, highly crystalline silk fibroin particles as claimed in claim 1, and further comprising one or more additional additives.

6. The composition as claimed in claim 5, wherein the one or more additional additives are present in the composition at a concentration in the range of 1-70% by weight.

7. The composition as claimed in claim 5, wherein the one or more additional additives are selected from the group consisting of ceramic fillers, natural and synthetic fiber reinforcements, and other biomolecules.

8. The composition as claimed in claim 5, wherein said composition comprising the one or more additives is in the form of a gel, a hydrogel, a paste, a lotion, a cream, an ointment, a foam, a spray, an aerosol, a scrub, or any combinations thereof.

9. The composition as claimed in claim 7, wherein the ceramic filler is selected from the group consisting of hydroxyapatite, beta tricalcium phosphate, calcium sulphate, and calcium phosphate.

10. The composition as claimed in claim 7, wherein the synthetic fiber reinforcement is selected from the group consisting of SF fibers, jute fibers, and polypropylene fibers.

11. The composition as claimed in claim 7, where the biomolecules are selected from the group consisting of drugs and growth factors.

12. A 3d scaffold prepared using the spherical highly crystalline silk fibroin particles as claimed in claim 1.

13. A method of using the 3d scaffold as claimed in claim 12, for biomedical applications, the method comprising the steps of:
   supplying the 3d scaffold and a biomedical composition, and
   introducing the 3d scaffold into the biomedical composition.

14. The spherical, highly crystalline silk fibroin particles as claimed in claim 1, where a d10/d90 of the particles is greater than 0.8.

15. The spherical, highly crystalline silk fibroin particles as claimed in claim 14, wherein the d10/d90 of the particles is in a range of 0.83 to 0.93.

16. The process for the preparation of spherical, highly crystalline silk fibroin particles as claimed in claim 4, where a d10/d90 of the particles is greater than 0.8.

17. The spherical, highly crystalline silk fibroin particles as claimed in claim 16, wherein the d10/d90 of the particles is in a range of 0.83 to 0.93.

\* \* \* \* \*